US00PP07952P

United States Patent [19]

Zaiger et al.

[11] Patent Number: Plant 7,952

[45] Date of Patent: Aug. 25, 1992

[54] PEACH TREE "SWEET GEM"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 637,801

[22] Filed: Jan. 7, 1991

[51] Int. Cl.[5] ..... A01H 5/00

[52] U.S. Cl. ..... Plt./43.1

[58] Field of Search ..... Plt./43

[56] References Cited

U.S. PATENT DOCUMENTS

P.P. 4,917 11/1982 Zaiger ..... Plt. 43

*Primary Examiner*—James R. Feyrer

[57] ABSTRACT

Our new development is a distinct variety of peach tree which has the following unique combination of features that are outstanding in a new variety:

1. Fruit with firm flesh having very good handling, shipping and storage quality.
2. Large size of fruit throughout the tree.
3. Fruit staying firm on tree 10 to 14 days after maturity.
4. Heavy and regular production of fruit.
5. Fruit with a high degree of attractive red skin color.
6. Producing mild, sub-acid fruit with good flavor and eating quality.
7. Vigorous, upright growth habit.

1 Drawing Sheet

ORIGIN OF THE VARIETY

The present variety of peach tree was developed by us in our experimental orchard located near Modesto, Calif., as a second generation seedling of a cross between two selected seedlings. The pollen parent originated from open pollinated seed of Sam Houston Peach (non-patented) and the female parent originated from a cross between May Grand Nectarine (U.S. Plant Pat. No. 2,794) and a peach of unknown parentage. A large number of second generation seedlings were grown and maintained under close observation, during which time we recognized the outstanding characteristics described above and selected the variety for reproduction and commercialization.

ASEXUAL REPRODUCTION OF THE VARIETY

Asexual reproduction of the new and distinct variety was performed by us in the experimental orchard located near Modesto, Calif., and shows that all characteristics run true to the original tree and are established and transmitted through succeeding propagations.

SUMMARY OF THE VARIETY

The present new variety is a new and distinct variety of peach tree which is of large size, vigorous upright in growth and a regular and productive bearer of large, very firm, yellow flesh, clingstone fruit with good flavor and eating quality. The fruit remain firm on the tree 10 to 14 days after maturity, and have good shipping and storage quality with a high degree of attractive red skin color.

DESCRIPTION OF THE PHOTOGRAPHS

The accompanying photographs show reproduction in color of typical specimens of the fruit and foliage of our new peach variety. The upper and lower surface of the leaves are shown, as are fruit specimens showing the exterior and a sectional view of a fruit divided in the suture plane to reveal flesh coloration and to show a stone remaining in place. The photographs were taken shortly after being picked at maturity (firm ripe) and the colors are as nearly true as is reasonably possible in a color representation of this type.

DESCRIPTION OF THE VARIETY

The following is a botanical detailed description of the new variety of peach tree, its fruit, flowers and foliage as based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigorous.*—Vigorous.
- *Form.*—Upright.
- *Density.*—Medium.
- *Shape.*—Usually pruned to vase shape.
- *Production.*—Productive.
- *Bearing.*—Regular bearer.

Trunk:
- *Size.*—Medium to large.
- *Texture.*—Medium shaggy.
- *Color.*—Grayish brown.

Branches:
- *Size.*—Medium.
- *Surface.*—Medium rough.
- *Lenticels.*—Numerous. Medium to large size.
- *Color.*—Brown to grayish brown.

Leaves:
- *Size.*—Large. Average length — 6". Average width — 1½".
- *Form.*—Lanceolate. Pointed.
- *Texture.*—Smooth.
- *Margin.*—Crenate.
- *Petiole.*—Medium length. Medium thickness.
- *Glands.*—Reniform. Number varies from 1 to 3. Average number 2. Medium size.
- *Color.*—Upper surface — green to dark green (27-F-6) to (27-F-8). Lower surface — dull green to grayish green (28-D-6) to (28-E-6).

Flower buds:
- *Size.*—Large.

*Shape.*—Plump.
*Pubescence.*—Pubescent.

Flowers:
*Size.*—Large — showy.
*Blooming period.*—Mar. 6, 1989 to Mar. 13, 1989. Varies slightly with climatic conditions.
*Pollen.*—Present.
*Color.*—Pink.

Fruit:
*Maturity when described.*—Firm ripe.
*Date of first picking.*—Jun. 10, 1989.
*Date of last picking.*—Jun. 16, 1989.
*Size.*—Large. Average diameter axially — 2⅞" to 3". Average transversely in suture plane — 2¾" to 2⅞".
*Form.*—Nearly globose. Slightly flattened at stem end. Slight apical point.
*Suture.*—Shallow — extends from base to apex.
*Ventral surface.*—Rounded, nearly smooth.
*Base.*—Retuse.
*Cavity.*—Rounded — some fruit slightly elongated in suture plane.
*Apex.*—Usually slight pistil point. Varies from slight pistil point to rounded.

Skin:
*Thickness.*—Medium.
*Texture.*—Medium.
*Tendency to crack.*—None.
*Down.*—Moderate — short.
*Color.*—Bright yellow ground color — (4-A-7) to (4-A-8). Overspread with red — (9-B-8) to (9-C-8).

Flesh:
*Ripens.*—Evenly.
*Texture.*—Firm.
*Fibers.*—Few and tender.
*Juice.*—Moderate.

*Flavor.*—Good, sub-acid sweet — very mild.
*Eating quality.*—Good.
*Amygdalin.*—Undetected.
*Color.*—Varies from light yellow (4-A-5) to rich golden yellow (4-A-7).

Stone:
*Type.*—Clingstone.
*Size.*—Medium. Average length — 1½". Average breadth — 1". Average thickness — ⅝".
*Form.*—Ovid.
*Base.*—Varies from straight to rounded.
*Sides.*—Equal to unequal.
*Apex.*—Acuminate.
*Surface.*—Irregularly furrowed toward apex pitted throughout, heavier toward base.
*Tendency to split.*—None.
*Color.*—Light brown to brown (6-B-6) to (6-C-6).

Use: Dessert.
*Market.*—Local and long distance.

Keeping quality: Good.
Shipping quality: Good.

The new and distinct variety of peach tree, its flowers and fruit may vary in slight detail due to climatic, soil conditions and cultural practices under which the variety may be grown; the present description is that of the variety grown near Modesto, Calif.

We claim:

1. A new and distinct variety of peach tree, substantially as illustrated and described, characterized by its large size, vigorous upright growth and being a productive and regular bearer of very firm, sub-acid, yellow flesh, clingstone fruit with good flavor and eating quality; the fruit is further characterized by having an attractive red skin color, staying firm on the tree 10 to 14 days after maturity and having good shipping and storage quality.

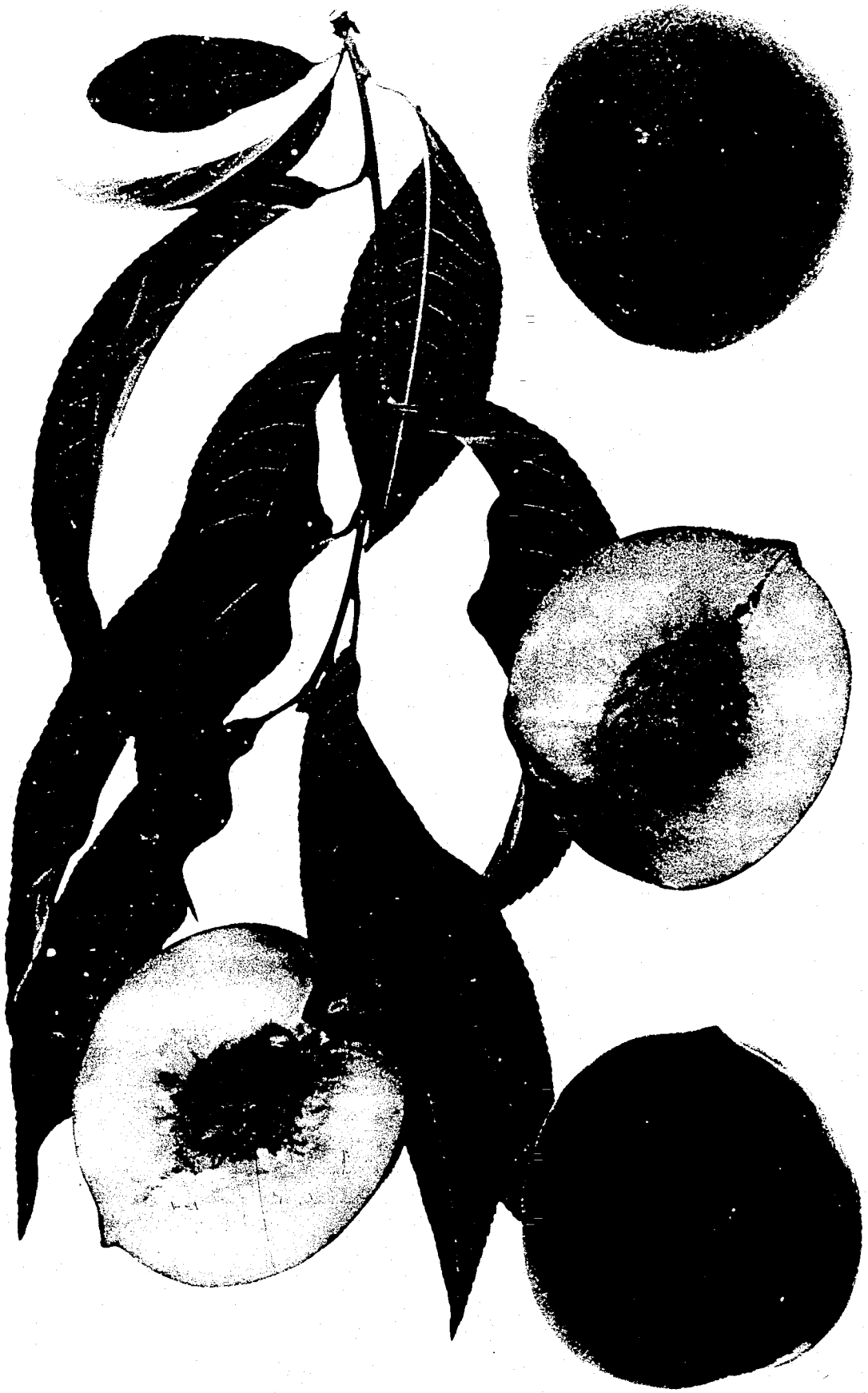

* * * * *